United States Patent [19]

Soule et al.

[11] Patent Number: 5,506,134
[45] Date of Patent: Apr. 9, 1996

[54] HYPRIDOMA AND MONOCLONAL ANTIBODY WHICH INHIBITS BLOOD COAGULATION TISSUE FACTOR/FACTOR VIIA COMPLEX

[75] Inventors: Howard R. Soule, Encinitas; Terence K. Brunck, San Diego, both of Calif.

[73] Assignee: Corvas International, Inc., San Diego, Calif.

[21] Appl. No.: 759,443

[22] Filed: Sep. 13, 1991

Related U.S. Application Data

[63] Continuation-in-part of Ser. No. 601,454, Oct. 22, 1990, abandoned.
[51] Int. Cl.$^6$ ............................. C12N 5/12; C07K 16/00; C07K 16/18
[52] U.S. Cl. .............................. 435/240.27; 530/387.1; 530/388.1; 530/388.25
[58] Field of Search ................................ 530/388.25, 387.1, 530/388.1, 388.25; 435/240.27, 70.21

[56] References Cited

U.S. PATENT DOCUMENTS 4,382,083 5/1983 Thomas ................................ 424/101

FOREIGN PATENT DOCUMENTS

| 0136835 | 9/1984 | European Pat. Off. . |
| WO91/07432 | 5/1991 | European Pat. Off. . |
| 8912469 | 12/1989 | WIPO . |

OTHER PUBLICATIONS

Carson et al., Blood, 70:490–493, Aug. 1987.
Takase, et al., J. Clin Pathol, 41:337–341, 1988.
Warr et al., 75 Blood 1481, 1990.
Carson et al., 66 Blood 152, 1985.
Drake et al., 134 American Journal of Pathology 1807, 1989.
Drake et al., 109 Journal of Cell Biology 389, 1989.
"Preliminary Characterization of a Panel of Monoclonal Antibodies to Human Factor VII", Coppola et al., *Curr. Stud. Hematol. Blood Transfus.* (1991) 58:187–193.
"Monoclonal Antibody (VII–M31) to Bovine Factor VII: A Specific Epitope in the γ-Carboxyglutamic Acid Domain"; Higashi et al., *J. Biochemistry* (1990) 108:654–662.
Waldman, *Science* 252:1657–1662 (1991).

*Primary Examiner*—Margaret Parr
*Assistant Examiner*—Susan A. Loring
*Attorney, Agent, or Firm*—Lyon & Lyon

[57] ABSTRACT

Coagulation protein antagonists are disclosed, which include monoclonal-type antibodies and related cell lines disclosed for the production of specific, neutralizing antibodies against factors VII and VIIa and the tissue factor/factor VIIa bimolecular complex, which antibodies are useful for the prevention or treatment of thrombotic and related diseases, for immunoaffinity isolation and purification of factors VII and VIIa and the tissue factor/factor VIIa complex, and for determination of factors VII or VIIa and the tissue factor/factors VII or VIIa complex in a biological sample.

3 Claims, 4 Drawing Sheets

HYBRIDOMA AND MONOCLONAL ANTIBODY WHICH INHIBITS BLOOD COAGULATION TISSUE FACTOR/FACTOR VIIA COMPLEX

RELATED APPLICATIONS

This application is a continuation-in-part of Soule and Brunck, entitled "Blood Coagulation Protein Antagonists And Uses Therefor", filed Oct. 22, 1990, U.S. Ser. No 07/601,454, now abandoned and hereby incorporated by reference herein, including the drawings attached thereto.

FIELD OF THE INVENTION

The present invention relates to antibodies and functional fragments thereof and, more particularly, to the treatment of patients for thrombotic disease or the prevention of thrombotic disease using anti-thrombotic agents including immunoglobulin protein and protein fragments or derivatives directed to certain blood coagulation-related proteinaceous antigens and epitopic regions thereof.

BACKGROUND OF THE INVENTION

Hemostasis is a naturally occurring process which results in the spontaneous arrest of bleeding from damaged blood vessels. For example, precapillary vessels will contract immediately when an individual is cut. Within seconds after such a cut, the process of hemostasis begins. At a site of injury with disruption of a blood vessel or exposure of subendothelial vascular tissue, two events rapidly occur. The two limbs of the hemostatic system, each comprised of many molecules, are activated. The coagulation (clotting) system is immediately initiated producing thrombin; and blood platelets adhere to matrix proteins. The platelets are activated, in part by thrombin, and release adenosine diphosphate ("ADP") leading to aggregation of additional platelets into a growing platelet plug in concert with the conversion of fibrinogen in the blood to the insoluble fibrin gel. This hemostatic plug is strengthened by additional enzymatic cross-linking. Over time it is dissolved during tissue repair to result in normal tissue and blood vessel, with or without residual pathology of the local vessel wall or tissue.

Thrombogenesis is an altered, pathogenic state of one or both limbs of the hemostatic system. In such states, an intravascular (arterial or venous) thrombus results from a pathological disturbance of hemostasis. A platelet-rich thrombus, for example, is thought to be initiated by the adhesion of circulating platelets to the wall of an arterial vessel. This initial adhesion, activation by thrombin or other agonists, and the concomitant release of ADP from platelets, is followed by platelet-platelet interaction or aggregation. Fibrin formation is associated with the platelet thrombus but is a minor component. The arterial thrombus can grow to occlusive proportions in areas of slower blood flow.

In contrast, fibrin-predominant thrombi develop initially in areas of stasis or slow blood flow in blood vessels and may resemble a blood clot formed in vitro. The bulk of venous thrombi comprise a fibrin network enmeshed with red blood cells and platelets. A venous thrombus can establish a "tail" that can detach and result in embolization of the pulmonary arteries. Thus, it will be understood that arterial thrombi cause serious disease by local ischemia, whereas venous thrombi do so primarily by distant embolization.

A platelet plug formed solely by ADP-stimulating platelet interaction is unstable. Immediately after the initial aggregation and viscous metamorphosis of platelets, as noted above, fibrin becomes a constituent of a platelet-rich thrombus. Production of thrombin occurs by activation of the reactions of blood coagulation at the site of the platelet mass. This thrombin may activate the initial adherent platelets and stimulates further platelet aggregations. Platelet aggregation is stimulated not only by inducing the release of ADP from the platelets, but also by stimulating the synthesis of prostaglandins, which as aggregating agents are more powerful than ADP, and by the assembly of the prothrombinase complex on the activated platelets to accelerate the formation of more thrombin, the very powerful activator of platelets.

The coagulation of blood results in the formation of fibrin. It involves the interaction of more than a dozen proteins in a cascading series of proteolytic reactions. At each step a clotting factor zymogen undergoes limited proteolysis and itself becomes an active protease. This clotting-factor enzyme activates the next clotting factor zymogen until thrombin is formed which connects fibrinogen to the insoluble fibrin clot. The blood clotting factors include factor I (fibrinogen), factor II (prothrombin), tissue factor (formerly known as factor III), factor IV ($Ca^{2+}$), factor V (labile factors), factor VII (proconvertin), factor VIII (antihemophilic globulin, or "AHG"), factor IX (Christmas factor), factor X (Stuart factor), factor XI (plasma thromboplastin antecedent, or "PTA"), factor XII (Hageman factor), factor XIII (fibrin-stabilizing factor), and factors HMW-K (high-molecular-weight kininogen, or Fitzgerald factor), PRE-K (prekallikrein, or Fletcher factor), Ka (kallikrein), and PL (phospholipid).

Fibrinogen is a substrate for the enzyme thrombin (factor IIa), a protease that is formed during the coagulation process by the activation of a circulating zymogen, prothrombin (factor II). Prothrombin is converted to the active enzyme thrombin by activated factor X in the presence of activated factor V, $Ca^{2+}$, and phospholipid.

Two separate pathways, called the "intrinsic" and "extrinsic" systems, lead to the formation of activated factor X. In the intrinsic system, all the protein factors necessary for coagulation are present in the circulating blood. In the extrinsic system, tissue factor, which is not present in the circulating blood, is expressed on damaged endothelium, on activated monocytes by cells in the arteriosclerotic plaque or by cells outside the vessel wall. Tissue factor then acts as the receptor and essential cofactor for the binding of factor VII resulting in a bimolecular enzyme to initiate the extrinsic pathway of coagulation. This mechanism also activates the intrinsic pathway of coagulation. The tissue factor pathway can very rapidly clot blood.

Blood can also be clotted by the contact system via the intrinsic pathway of coagulation. The mechanism is somewhat slower than the tissue factor pathways, presumably because of the larger number of reactions that are required. Both the intrinsic system and extrinsic system pathways must be intact for adequate hemostasis. See Zwaal, R. F. A., and Hemker, H. C. "Blood cell membranes and hemostasis." Haemostasis, 11:12–39 (1982).

Thrombosis and a variety of related forms of diseases are associated with, and result from, activation of one or more of the coagulation protease cascades pathways, and disorders of regulation of the combined coagulation/anticoagulation/fibrinolytic pathways. These diseases affect approximately 2.5 million individuals annually in the United States.

Some three percent of the U.S. population over the age of 45 develop some form of thrombotic disease or disseminated coagulation each year. Other thrombotic diseases are hereditary and may affect 100,000 people annually. Seventy percent of such diseases are fatal by 45 years of age.

Of acquired thrombotic diseases, coronary thrombosis at about 1.5 million cases per year, pulmonary thromboembolism at about 400,000 cases per year and severe septic shock at more than 300,000 cases per year, disseminated intravascular coagulation (DIC) at about 350,000 cases per year, and deep vein thrombosis at about 175,000 cases per year, predominate. However, diseases such as menigococemia, hemorrhagic fever virus infections, and a variety of other diseases produce significant morbidity and mortality as well. See, e.g., Kaplan, K. "Coagulation Proteins in Thrombosis." In *Hemostasis and Thrombosis*, Colman, R. W., et al. eds., pages 1098 et seq. (2d Ed. J. B. Lippincott Co. 1987). Some of the most acutely severe forms of disseminated intravascular coagulation affect children secondary to a variety of infectious diseases. Current treatment for thromboembolic disease is by no means satisfactory, and includes the use of anticoagulants, antithrombotic drugs and thrombolytic agents.

One of the most well-known anticoagulants is heparin. Discovered in 1922, heparin is a heterogenous group of straight-chain anionic mucopolysaccharides, called glycosaminoglycans, of molecular weights that average 15,000 daltons. Commercial heparin typically consists of polymers of two repeating disaccharide units: D-glucosamine-L-iduronic acid and D-glucosamine-D-glucuronic acid. It is typically prepared from both bovine lung and porcine intestinal mucosa, and has also been obtained from sheep and whales.

While heparin occurs intracellularly in mammalian tissues that contain mast cells, it is limited to a macromolecular form of at least 750,000 daltons. Furthermore, this heparin has only 10–20% of the anticoagulant activity of commercial heparin. Heparan sulfate, a compound similar to heparin but with less anticoagulant activity is a ubiquitous component at the mammalian cell surface. When native heparin is released from its bound and inactive state in the metachromatic granules of mast cells, it is ingested and rapidly destroyed by macrophages. Heparin cannot be detected in the circulating blood.

When injected intravenously, commercially prepared heparin impairs blood coagulation. It acts by complexing with antithrombin III, a serine protease inhibitor that neutralizes several activated clotting factors, i.e., factors XIIa, kallikrein (activated Fletcher factor), XIa, IX, Xa and thrombin (IIa). However, it is most active in inhibiting free thrombin and activated factor X (Xa). Although antithrombin III was thought to be the only macromolecule able to inactivate thrombin, other plasma proteins are now known to possess this activity. Antithrombin III can form irreversible complexes with serine proteases, and, as a result, the above protein factors are inactivated. Griffith, M. J. "Heparin-Catalyzed Inhibitors/Protease Reactions: Kinetic Evidence for a Common Mechanism of Action of Heparin," *Proc. Natl Acad Sci USA*, 80:5460–5464 (1983). Heparin markedly accelerates the velocity, although not the extent of this reaction. A ternary complex is apparently formed between heparin, antithrombin III, and the clotting factors. Bjork, I., and Lindahl, U. "Mechanism of the Anticoagulant Action of Heparin" *Mol. Cell. Biochem.*, 48:161–182 (1982). Low concentrations of heparin increase the activity of antithrombin III, particularly against factor Xa and thrombin and this forms the basis for the administration of low doses of heparin as a therapeutic regimen.

While purified commercial preparations of heparin are relatively non-toxic, a chief complication of therapy with heparin is hemorrhage. Heparin also causes transient mild thrombocytopenia in about 25% of the patients, severe thrombocytopenia in a few, and occasional arterial thrombi. The mild reactions result from heparin-induced platelet aggregation, while severe thrombocytopenia follows the formation of hepar-independent antiplatelet antibodies complexes. It is to be understood that, in all patients given heparin, platelet counts must be monitored frequently, any new thrombi might be the result of the heparin therapy, thrombocytopenia sufficient to cause hemorrhage should be considered to be heparin-induced, and that thrombosis thought to result from heparin should be treated by discontinuation and substitution of an agent that inhibits platelet aggregation and/or an oral anticoagulant.

Severe thrombocytopenia, hemorrhage, and death have occurred even in patients receiving "low-dose" heparin therapy. Heparin therapy is, furthermore, contraindicated in patients who consume large amounts of ethanol, who are sensitive to the drug, who are actively bleeding, or who have hemophilia, purpura, thrombocytopenia, intracranial hemorrhage, bacterial endocarditis, active tuberculosis, increased capillary permeability, all sorts of lesions of the gastrointestinal tract, severe hypertension, threatened abortion, or visceral carcinoma. Furthermore, heparin is to be withheld during and after surgery of the brain, eye, or spinal cord, and is not to be administered to patients undergoing lumbar puncture or regional anesthetic block. *Goodman and Gillman's The Pharmacological Basis of Therapeutics*, pages 1339–1344 (7th ed. 1985).

There are a number of oral anticoagulants that are also available for clinical use. Many anticoagulant drugs have been synthesized as derivatives of 4-hydroxycoumarin or of the related compound, idan-1,3-dione. The essential chemical characteristics of the coumarin derivatives for anticoagulant activity are an intact 4-hydroxycoumarin residue with a carbon constituent at the 3 position. There are a number of differences in the pharmacokinetic properties and toxicities of these agents, however, and racemic warfarin sodium is the most widely used oral anticoagulant in the United States.

The major pharmacological effect of oral anticoagulants is inhibition of blood clotting by interference with the hepatic post translational modification of the vitamin K-dependent proteins among which are the clotting factors, i.e., Factors II, VII, IX and X. These drugs are often called indirect anticoagulants because they act only in vivo, whereas heparin is termed a direct anticoagulant because it acts in vitro as well. Again, hemorrhage is the main unwanted effect caused by therapy with oral anticoagulants, and such therapy must always be monitored. In reported order of decreasing frequency, complications include ecchymoses, hematuria, uterine bleeding, melena or hematochezia, epistaxis, hematoma, gingival bleeding, hemoptysis, and hematemesis. All of the contraindications described above in regard to the use of heparin apply to the anticoagulants as well.

Anti-platelet drugs suppress platelet function and are used primarily for arterial thrombotic disease, whereas anticoagulant drugs, such as warfarin and heparin suppress the synthesis or function of clotting factors and are used to control venous thromboembolic disorders. There are a number of anti-platelet drugs, the most well-known being aspirin. The efficacy of these agents for acute treatment has, however, not been established and there is a real problem with aspirin hemorage.

Thrombolytic drugs include streptokinase, urokinase, tissue plasminogen activator, and APSAC (acylated plasminogen streptokinase complex). These are proteins which have demonstrated efficacy for the treatment of acute thrombotic disease. They promote the dissolution of thrombi by stimulating the conversion of endogenous plasminogen to plasmin, a proteolytic enzyme that hydrolyzes fibrin. The use of these agents is limited, however, to acute thrombotic disease. Fibrinolytic agents are used primarily for the treatment of patients with established coronary arterial thrombosis.

Effective therapy for a variety of forms of intravascular activation of the coagulation protease cascades, whether thrombosis or the more catastrophic forms such as those associated with vasomotor collapse (septic shock) and other forms of disseminated intravascular coagulations are not entirely satisfactory, and in the case of septic shock is entirely unsatisfactory. The need for effective therapy that is capable of rapidly arresting arterial thrombogenesis is recognized as an important therapeutic deficiency. This is evident from the recent evidence that heparin is entirely ineffective in preventing rethrombosis of the 11–20% of patients that rethrombose at the completion of thrombolytic therapy with tissue plasminogen activator.

The present invention was made in response to these needs and relates to antagonists of factor VII and specific antagonists of the procoagulant activity of factor VIIa and the tissue factor:factor VIIa complex. The invention includes monoclonal-type antibodies produced by cell systems including bacteria, such as E. coli, or by hybrid cell lines, characterized in that the antibodies, or functional fragments thereof, have predetermined specificity to factor VII, to factor VIIa, and/or to the bimolecular complex of tissue factor and factor VIIa, are effective for neutralization of these targets, and find application as antithrombotic agents for syndromes such as disseminated intravascular coagulation ("DIC") and venous thrombosis. The present invention also relates to the use of these monoclonal-type antibodies in methods for the purification of factor VII, factor VIIa and the bimolecular complex referred to above, and in methods for the immunoassay or immunodetection of factor VII, factor VIIa and the tissue factor/factor VIIa bimolecular complex. The purification of factor VII, factor VIIa and the tissue factor/factor VIIa complex from a biological sample containing these antigens can be carried out by immuno-affinity chromatography in which the biological sample is passed through an immunoadsorbant column or slurry comprising the novel monoclonal-type antibodies or antibody fragments of this invention bound to a solid base support to thereby selectively adsorb said antigenic targets. The immunoassay of factor VII, factor VIIa and the tissue factor/factor VIIa bimolecular complex for determining the presence or concentration of these target antigens in a biological sample containing them can be carried out by contacting said sample with a known amount of the novel monoclonal-type antibody of this invention and measuring the resulting adsorbed monoclonal antibody.

Factor VII is a vitamin K-dependent zymogen of the active serine protease VIIa. Factor VII functions to form a complex with tissue factor in blood, and on conversion to VIIa forms the complex which then activates factor X by converting factor X to factor Xa. Procoagulant activity is only associated with the tissue factor:VIIa complex. Free factor VII and free factor VIIa, as well as the tissue factor::factor VII complex, do not possess procoagulant activity. Factor VII is a single polypeptide chain of about 50,000 daltons that can, in a purified system, be activated by proteolytic cleavage of disulfide bonds by factor Xa, factor IXa, thrombin and factor XIIa. Takase, T. et al., "Monoclonal Antibodies to Human Factor VII: A One Step Immunoradiometric Assay for VIIag, *J. Clin. Pathol.*, 41:337–341 (1988). Human factor VII, when partially or completely activated, yields a protein comprised of two polypeptide chains linked by disulfide bridges. Factor VII and VIIa may be used interchangeably in this document and will be designated VII/VIIa when target interchangeability is to be indicated.

With the advent of hybridoma technology first developed by Kohler and Milstein, it is now possible to attempt to generate monoclonal antibodies which are essentially homogenous compositions having uniform affinity for a particular binding site. The production of mouse hybridomas by these investigators is described in Nature, 256:495–497 (1975) and Eur. J. Immunol., 6:511–519 (1976). Further procedures are described in Harlow, E., and Lane D., "Antibodies: A Laboratory Manual" (Cold Spring Harbor Laboratory 1988). According to the hybridoma method, tissue-culture adapted mouse myelomas cells are fused to spleen cells from immunized mice to obtain the hybrid cells, called "hybridomas," that produce large amounts of a single antibody molecule. Generally, animals are injected with an antigen preparation, and if an appropriate humoral response has appeared in the immunized animal, an appropriate screening procedure is developed. The sera from test bleeds of the immunized animal are used to develop and validate the screening procedure, and after an effective screen has been established, the actual production of hybridomas is begun. Several days prior to the fusion, which is generally carried out in the presence of polyethylene glycol as described by Galfe et al. Nature, 266:550–552 (1977), followed by selection in HAT medium (hypoxanthine, aminopterin and thymidine) as described by Littlefield, Science, 145:709–710 (1964), animals are boosted with a sample of the antigen preparation. For the fusion, antibody secreting cells are prepared from the immunized animal, mixed with the myeloma cells, and fused. After the fusion, cells are diluted in selective medium and plated in multi-welled culture dishes. Hybridomas may be ready to test as soon as about one week after the fusion, but this is not certain. Cells from positive wells are grown, subcloned, and then single-cells are cloned.

It is understood that hybridoma production seldom takes less than two months from start to finish, and can take well over a year. The production of monoclonal antibodies has been described in three stages: (1) immunizing animals (2) developing the screening procedure and (3) producing hybridomas. It is also understood that any one of these stages might proceed very quickly but that all have inherent problems. For example, while immunization can be carried out with virtually any foreign antigen of interest, many difficulties arise and variations may be required for any specific case in order to generate the desired monoclonal antibodies. Prior to attempting to prepare a given hybridoma, there is no assurance that the desired hybridoma will be obtained, that it will produce antibody if obtained, or that the antibody so produced will have the desired specificity or characteristics. Harlow, E., and Lane, D., supra at Chapter 6.

The production of monoclonal antibodies to human factor VII has been reported, and these reagents are said to have been used to make immunodepleted plasma or to detect factor VII cross reactive material in factor VII deficient patients. Id. The production of monoclonal antibodies to factor VII for their use in a one step, immunoradiometric assay for factor VII:ag has also been reported. Id. The authors reported the preparation of three mouse monoclonal antibodies, two of which were said to bind, to factor VII:ag, and two of which were said to be inhibitors of factor VII in vitro. See also Howard et al., J. Clin. Chem., 35:1161 (1989). No monoclonal antibodies against either factor VII or factor VIIa have been described which therapeutically interfere with the binding of factor VIIa to tissue factor or which neutralize the activity of the tissue factor/factor VIIa complex.

BRIEF SUMMARY OF THE INVENTION

In accordance with the present invention novel monoclonal-type antibodies or antibody fragments are provided which can be produced by recombinant cell lines or by hybrid cell lines, the antibodies being characterized in that they have certain predetermined specificity to particular targets, i.e., factor VII, factor VIIa, the bimolecular complex of tissue factor and factor VIIa, and to particular epitopic regions thereof, and have neutralizing capability when combined with these targets. By virtue of their binding to factors VII and VIIa as competitive, non-functional surrogates of tissue factor, they serve as antagonists to neutralize the functional activation of the coagulation protease cascades. These antibodies are useful in the prevention and therapeutic treatment of thrombotic conditions and related diseases in which the activation of the above coagulation protease cascades plays a significant pathogenic role. Particular antibodies are also useful in methods for the purification of factors VII and VIIa and the tissue factor/factor VIIa bimolecular complex, and in the immunoassay of these target antigens.

Accordingly, the present invention also provides a method of preventing or treating a mammalian species for an incipient or existing thrombotic disease condition that would be alleviated by an agent that selectively interferes with the extrinsic coagulation cascade, which comprises administering to a mammalian species in need of such treatment a prophylactically or therapeutically effective amount of a tissue factor:factor VIIa complex antagonist. The present invention provides for the prevention or treatment of thrombotic disease conditions including acute disseminated intravascular coagulation, septic shock, coronary thrombosis, organ transplant rejection, and deep vein thrombosis. Effective tissue factor:factor VIIa complex antagonists include monoclonal-type antibodies, preferably monoclonal antibodies or fragments thereof, having the tissue factor:factor VIIa complex antagonist characteristics of antibodies produced by hybridoma cell line ATCC HB 10558. The invention further provides for monoclonal antibodies having the ability to complex with all or some portion of a loop region on the factor VII/VIIa molecule, preferably the structural loop region which comprises the amino acids 195–208 on the factor VII/VIIa molecule.

The invention also provides for compositions useful in the prevention or treatment of a thrombotic disease condition which comprises an effective amount of a tissue factor:factor VIIa complex antagonist. Such compositions may include the monoclonal antibodies and/or monoclonal antibody fragments referenced above. The invention further provides for substantially purified and purified preparations of monoclonal antibodies or monoclonal antibody fragments which substantially inhibit the procoagulant activity of the tissue factor:factor VIIa complex. The present invention also provides for hybridoma cell lines which permit the production of such monoclonal antibodies and monoclonal antibody fragments. Methods for producing such hybridoma cell lines are also described and claimed herein that comprise immunizing an animal species with an immunogen comprising one or more factor VIIa structural loop region peptides.

Methods for inhibiting the procoagulant activity of the tissue factor:factor VIIa complex in vivo are also described and claimed, which comprise administering to a mammalian species a monoclonal-type antibody or antibody fragment that specifically reacts with said complex but does not substantially inhibit free factor VIIa.

The factor VIIa and the tissue factor/factor VIIa bimolecular complex against which the monoclonal-type antibodies of this invention have specificity can be isolated from biological samples in the methods described herein.

BRIEF DESCRIPTION OF THE DRAWINGS

While the specification concludes with claims particularly pointing out and distinctly claiming the subject matter regarded as forming the present invention, it is believed that the invention will be better understood from the following description taken in connection with the accompanying drawings in which:

DETAILED DESCRIPTION OF THE INVENTION

Figure 1:
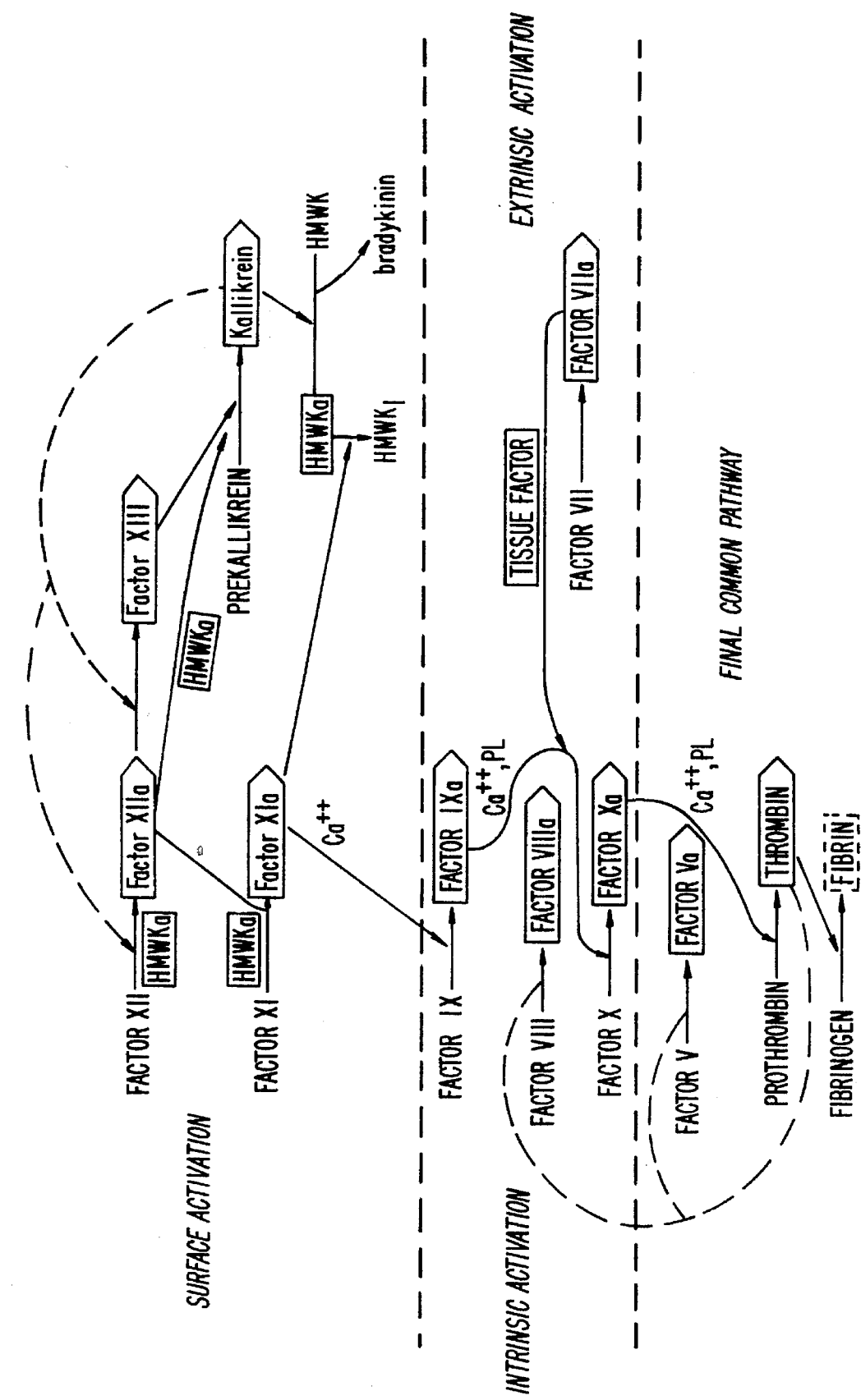
FIG. 1 is a schematic representation of the clotting cascade, divided into those sequences involved in surface (contact) activation, intrinsic and extrinsic activation, and the final common pathway. Solid lines indicate direct activation of precursor zymogen to enzyme; interrupted lines show paths of both positive and negative feedback. PL indicates phospholipid.

As specifically shown in FIG. 1, blood coagulation can begin when the Hageman factor (XII) undergoes contact activation and becomes bound to surfaces. This surface-bound factor XII undergoes proteolytic activation by kallikrein (Ka) in the presence of a high-molecular-weight kininogen (HMW-K). This surface activation (contact system, intrinsic pathway) appears to initiate coagulation in vitro but is not considered to be a relevant in vivo mechanism. Deficiencies in this pathway (XII, prekallikrein and HMWK) result in prolonged in vitro clotting times but do not cause hemostatic disorders.

Factor XIIa constitutes an arm of a feedback loop and activates more Ka from prekallikrein (Pre-K or Fletcher factor), in the presence of HMW-K. Factor XIIa in the presence of HMW-K also activates factor XI. Factor XIa in the presence of $Ca^{2+}$ proteolytically activates factor IX to IXa. Factor VIII, factor IXa, $Ca^{2+}$, and phospholipid micelles (PL) from blood platelets form a lipoprotein complex with factor X and result in factor X activation. Factor V, factor Xa, $Ca^{2+}$, and PL also form a lipoprotein complex with factor II or prothrombin and activate it to IIa or thrombin. In seconds, thrombin splits two small pairs of peptides off the large fibrinogen molecule, followed by rapid noncovalent aggregation of soluble fibrin monomers. Factor XIII, activated by thrombin to XIIIa, cross-links adjacent fibrin monomers covalently to form the insoluble fibrin clot.

There is considerable evidence that tissue factor initiates coagulation in the generalized Schwartzman reaction (DIC) resulting from endotoxinemia. Kaplan, K. Coagulation Proteins in Thrombosis. In "Hemostasis and Thrombosis" (Colman, R. W., Hirsh, J., Marder, V. J., and Salzman, E. W.; eds.) 2nd Ed. J. B. Lippincott Co., pp. 1098, 1987. Fibrin microthrombi are uniformly found in fatal DIC and thrombosis of large arteries and veins may be found in 40% of cases. Minna, J. D., Robboy, S. J., Colman, R. W. Disseminated Intravascular coagulation in Man. C. C. Thomas, 1974. Leukocytes are required participants and are induced by endotoxin to a procoagulant (thrombogenic) state, Semararo, N , et al , . "Role of leukocyte procoagulant activity in endotoxin-induced DIC: Evidence from comparative studies in rats and rabbits." Agents Actions 11:646, 1981, 26, expressing tissue factor. Colucci, M., "Cultured human endothelial cells generate tissue factor in response to endotoxin." *J. Clin. Invest.* 73:1893, 1983. At the same time endothelial cells are also induced to express tissue factor, initiate coagulation and to depress their anticoagulant properties. Moore, K. L., "Endotoxin enhances tissue factor and suppresses thrombomodulin expression of human vascular endothelium in vitro." J. Clin. Invest. 79:124–130, 1987.

The extrinsic coagulation cascade as currently envisioned starts with the formation of the tissue factor:VII and tissue factor:VIIa complexes on the surface of tissue factor expressing cells. Tissue factor is not normally expressed by blood cells or vascular endothelial cells, but following stimulation with LPS, TNFalpha or IL-1, endothelial cells transcribe and express this molecule. Though fewer molecules of tissue factor are expressed, factor VII is bound and rapidly converted to factor VIIa by factor Xa feedback activation of the bound factor VII. Endothelial cell factor IX/IXa receptor (IX-R) and factor VIII (activated to factor VIIIa by Xa or thrombin feedback) markedly enhance the kinetics of factor Xa generation by limited proteolytic activation of factor X. Cell surface associated factor V (activated by thrombin feedback) further amplifies the Vmax of factor Xa and prevents inhibition by plasma heparin:AT-III inhibitor. Prothrombin is efficiently converted to thrombin to convert fibrinogen to fibrin, leads to release of Plasminogen activator inhibitor I, serves as a chemotactic agent, aggregates platelets, activates Mac-1 receptor of monocytes, and has other inflammatory effects.

There are no presently effective drugs for the inhibition of the extrinsic pathway. The use of heparin, shown to be without benefit, is nevertheless continued clinically with the attendant secondary problems of its platelet effects. In DIC with depletion of antithrombin III there is no benefit to heparin since it is not a direct anticoagulant, only a cofactor for the thrombin inhibitor antithrombin III when present as a [heparin:antithrombin-III] complex. Anti-platelet drugs do not inhibit the coagulation protease cascade, and they diminish the necessary hemostatic properties of platelets. Warfarin therapy to interfere with Vitamin K supported gamma carboxylation of factors VII, X, IX and prothrombin is too slow and is associated with reduced activity of the natural anticoagulation pathways due to inhibition of gamma carboxylation of Protein C and Protein S. The present invention addresses this need by inhibiting the reaction pathway at the earliest possible step, the initiating proteolytic complex of tissue factor:VIIa, which will block the intravascular initiation of coagulation by tissue factor positive cells, e.g., endothelial cells, monocytes, and tissue factor positive foam cells in atherosclerotic plaques.

The present invention employs a neutralizing antagonist surrogate cofactor, preferably a monoclonal antibody or antibody fragment, to the functional bimolecular initiation complex of tissue factor and VII/VIIa and, more preferably, to a neoantigen(s) induced on the bimolecular tissue factor-:VIIa complex or alternatively, a neutralizing monoclonal antibody to VII or VIIa, preferably to a structural loop region thereof. Binding of such monoclonal antibodies to tissue factor:VIIa so as to block the active site of VII/VIIa, dissociate VIIa from tissue factor or competitively inhibit the association of the substrate serine protease zymogens factors X or IX will inhibit initiation of coagulation on vascular cells and arrest one of the major pathogenetic processes in thrombotic diseases.

Though the activation of coagulation has long been recognized as central and required for thrombus formation and growth and for disseminated intravascular coagulation, many mechanisms are put into action, particularly in the most virulent forms of septic shock. It has been demonstrated that monoclonal antibodies to TNFalpha are capable of protecting baboons from endotoxin mediated septic shock, Tracey K. J., "Anti-cachectin/TNF monoclonal antibodies prevent septic shock during lethal bacteraemia." *Nature* 330:662, 1987, since TNFalpha is induced by endotoxin, IL-1 and the toxic shock toxin 1. Michie, H. R., "Detection of circulating tumor necrosis factor after endotoxin administration." N. Eng. J. Med. 318:1481, 1988, Jupin, C., et al., "Protein C prevents the coagulopathic and lethal effects of escherichia coli infusion in the baboon." *J. Clin. Invest.* 79:18, 1987. However, anti-TNFalpha or anti-LPS monoclonal antibodies may have low efficacy once the pathologic process has been established. Recently, it has been shown that activated protein C, the natural anticoagulant protein given in massive doses is capable of arresting and even reversing early ongoing septic shock. Taylor, F. B., "Protein C prevents the coagulopathic and lethal effects of escherichia coli infusion in the baboon." *J. Clin. Invest.* 79:918, 1987. Now, evidence from the same group with the same model indicates that arresting the initiation of coagulation with monoclonal antibody to tissue factor is effective in treating septic shock in lethal challenge of baboons with E. coli (Edgington, et al., "Tissue Factor: Molecular Biology and Significance in the Pathophysiology of Gram-Negative Septic Shock," In: *Microbiological, Chemotherapeutical and Immunological Problems in High Risk Patients.* E. Garaci, et al., Eds., Raven Press, New York, Vol. 61, pp. 29–37 (1989).

One method useful for the production of anti-protein antibodies involves the use of synthetic peptides from regions of the protein sequence occur on the surface of the protein to raise and/or screen for desirable antibodies. In the case of Factor VIIa however, there is no available experimental data on the structure. Only the amino acid sequence is known. Factor VIIa has some sequence and structural homology in its catalytic domain to several other proteases whose structures have been determined by X-ray crystallography. The sequences of these proteases were analyzed and the sequence of the catalytic domain of factor VIIa was compared. Regions of the factor VIIa molecule were discovered that were highly conserved in structure often representing the core structure of the protein, as well as regions that were more variable. The regions in sequence with variable structures, herein denominated "loops," were discovered on the surface of the catalytic domains.

Eleven loop regions were identified in the sequence of the catalytic domain of factor VIIa. The include peptides comprising amino acids 165–177, 195–208, 209–218, 234–248, 248–258, 263–278, 285–295, 313–321, 330–339, 348–360, and 367–390. A computer model of the structure of the catalytic domain of factor VIIa was constructed and the location of the structurally variable loops ascertained. One set of loops was discovered to be located near the catalytic site of factor VIIa, and another clustered around the activation site where various proteases cleave the enzymatically inactive single-chain form, factor VII, to the active two-chain form, factor VIIa.

Anti-factor VII/VIIa antibody epitopes targeted for neutralization, were used to generate antibodies subsequently determined to neutralize or inhibit the activity of Factor VIIa by binding to a loop region. When these loops are near the active site, binding of these antibodies blocks access, for example, to the site by substrates such as Factor X and thereby inhibits the function of factor VIIa. In this manner, antibodies are prepared that block the extrinsic coagulation pathway.

Description of hybridoma preparation and initial characterization of monoclonal antibodies against factor VII/VIIa and the tissue factor/factor VIIa complex, is set forth in Example 1 below. Parameters are described relating to preparation of the antigen, dose and form of antigen, route of inoculation and immunization protocol, hybridoma preparation, and the screening, isolation and initial characterization of monoclonal antibodies. The properties of a monoclonal antibody designated 12D10 (ATCC HB 10558) are set forth and described. The antibody was shown to bind factor VII/VIIa and to dramatically inhibit the activity of the tissue factor:factor VIIa complex. As shown by the results in Example 2, the 12D10 antibody was also able to inhibit the activity of free factor VIIa. The 12D10 monoclonal antibody was shown in Example 3 to be specific to amino acids 195–208 region of the factor VII/VIIa molecule. Fragmentation of the 12D10 monoclonal antibody as described in Example 5, furthermore, was beneficially shown not to affect its clotting inhibition activity.

Antibodies, or the desired binding portions thereof including F(ab) and Fv fragments, can also be generated using processes which involve cloning an immunoglobulin gene library in vivo. Huse et al , . "Generation of a Large Combinatorial Library of the Immunoglobulin Repertoire in Phage Lambda," *Science* 246:1275–1281 (Dec. 8, 1989). Using these methods, a vector system is constructed following PCR amplification of messenger RNA (mRNA) isolated from spleen cells with oligonucleotides that incorporate restriction sites into the ends of the amplified product. Separate heavy chain and light chain libraries are constructed and may be randomly combined to coexpress these molecules together and screened for antigen binding. Single chain antibodies may also be prepared and utilized.

Additional monoclonals that neutralize the factor VIIa-tissue factor bimolecular cell surface activation complex can be made and selected from three classes of antithrombotic monoclonal antibodies. The specificity of the three classes of antibody include those reactive with factor VII and VIIa and neutralize amidolytic activity. Two subsets of antibody are generated. One will inhibit factor VIIa activity by preventing the association of tissue factor and factor VII/VIIa and the other will directly inhibit the activity of factor VIIa. The second class includes those monoclonals reactive with only Factor VIIa and neutralize amidolytic activity, while the third includes those reactive with neutralizing neoepitopes expressed as the result of association of tissue factor and factor VII. These neoepitopes would not be expressed on either free tissue factor or factor VII and therefore restricted to the coagulation initiation complex.

Each of the three classes of antibody represent further unique mechanistic approaches for antithrombotic therapy. Antibodies in the first class are defined by the specificity of the 12D10 monoclonal. Antibodies in the second specificity class are developed by immunizing mice with recombinant factor VIIa. Monoclonals that react with factor VIIa but not factor VII are selected. The desirable reagent will inhibit activity of preformed tissue factor:factor VIIa complexes. Neoepitopes expressed on the functional bimolecular complex will be immunogenic targets for the development of monoclonals that neutralize activity. These antibodies are prepared by performing in vitro immunization of murine splenocytes using preformed complexes of tissue factor:factor VIIa in an optimal environment of phospholipids. In vitro immunization is preferred due to the proteolytically labile nature of the complex in vivo; however, standard in vivo immunization of heparinized mice can also be employed. Screening is used to identify only those antibodies reactive with the tissue factor:factor VIIa complex, as opposed to those that are reactive with either free tissue factor factor VIIa. These antibodies will only inhibit coagulation at the site of injury or activation and normal hemostasis will not be compromised.

EXAMPLE 1

Preparation of hybridomas and identification of desired monoclonal antibodies was as follows. Female balb/c mice were immunized with purified human factor VII (factor VII) isolated from pooled human plasma over a period of approximately six months. Complete Freund's adjuvant was used for primary immunization and incomplete Freund's adjuvant for booster immunization. One to ten micrograms of protein was used per immunization. Route of immunization was both intraperitoneal and subcutaneous. Three days prior to fusion mice received an intravenous perfusion boost of purified factor VII (20 μg) in saline. Spleens were removed and spleen cells were fused to the SP2/0 myeloma following standard hybridoma methods.

The screening strategy employed a three-staged methodology. Primary screening identified hybridoma antibodies that reacted with factor VII or factor VIIa antigen. Secondary screening identified antibodies capable of inhibiting the functional activity of factor VIIa as indirectly assessed in a factor X activation chromogenic substrate assay. Tertiary screening assessed clotting inhibition of recalcified plasma in a two-stage prothrombin time test.

The primary screening assay was a radioimmunoassay where antibodies were tested for binding to $^{125}$I-factor VII. Briefly, ninety-six well polyvinyl chloride microliter plates were passively coated with affinity purified goat anti-mouse IgG obtained from Sigma Chemical Company, St. Louis, Mo. Antibodycoated plates were blocked with bovine albumin and culture supernatants (diluted at least 1:50) were bound to the plates. Plates were washed to remove unbound antibody and $^{125}$I-factor VII or factor VIIa (100,000 cpm/well; specific activity of factor VII=6 μi/μg; specific activity factor VIIa=4 μCi/μg) was added followed by incubation. Plates were washed to remove unbound factor VII and wells were transferred to a gamma counter to determine bound labeled factor VII. Negative controls include hybridoma culture supernatant from a cell line secreting irrelevant monoclonal antibody such as anti-tPA, sterile culture medium and buffer. Competition of binding of $^{125}$I-factor VII to antibody with excess unlabeled ligand is used to further demonstrate specificity.

The second screening was used to evaluate the ability of isolated antibodies to inhibit tissue factor catalyzed factor VII activity as reflected by the conversion of factor X to factor Xa. The human bladder carcinoma cell line J-82 (ATCC HTB-1) expresses cell surface-associated tissue factor and is used as the source of tissue factor and phospholipids. A chromogenic substrate for factor Xa is used, which develops color proportional to the amount of factor VIIa activity. Conversely, color is not developed if factor VII activity is blocked. The assay is performed as follows. J-82 cells are suspended in tris-buffered saline at a concentration of $1 \times 10^5$ cells per mL. Fifty microliters of cell suspension is added to individual wells of a 96-well polystyrene microliter plate. Fifty microliters of hybridoma culture supernatant diluted at least 1:10 is added to appropriate wells followed by 25 μL of 20 mM $CaCl_2$. Negative control is irrelevant hybridoma culture supernatant (such as anti-tPA supernatant) and positive control is 1 μM PPACK (d-phenylalanine-proline-arginine-chloromethylkefone). Twenty-five microliters of 90 nM factor X and 50 λL of substrate Spectrozyme Xa are added to each well. Following thirty minute incubation at room temperature, OD-405 is determined. Maximum activation (negative control) was obtained with samples that were treated with buffer or irrelevant hybridoma culture supernatant. Complete inhibition (positive control) assessed with the PPACK from this assay is shown in Table 1 below.

TABLE 1

| Results of Factor X activation assay | |
|---|---|
| Sample Treatment | OD-405 |
| Buffer | 1.101 |
| Anti-tPA hybridoma culture supernatant (1:10) | 1.151 |
| PPACK (1 μM) | 0.023 |

The properties a monoclonal antibody isolated from a preferred hybridoma, designated 12D10, in the factor VII/VIIa binding assay and the factor X activation assay are show in Tables 2 and 3 below. The 12D10 cell line was deposited with the American Type Culture Collection, 12301 Parklawn Drive, Rockville, Md. 20852, on Sep. 25, 1990, under the provisions of the Budapest Treaty.

TABLE 2

| Identification of Hybridoma ANtibody 12D10 in F.VII/VIIa Antigen Binding Assay | | |
|---|---|---|
| Antibody | $^{125}$I-rec Antigen | CPM Bound |
| 12D10 | rec* F.VII | 70397 |
| 12D10 | rec F.VIIa | 30489 |
| 12D10 | rec F.VII + 50-fold molar excess cold rec F.VII | 1878 |
| 12D10 | rec VIIa + 50-fold molar excess cold rec F.VIIa | 2771 |
| anti-tPA | rec F.VII | 5419 |
| anti-tPA | rec F.VIIa | 3734 |
| Culture medium | rec. F.VII | 2232 |
| Culture medium | rec VIIa | 4311 |

*rec = recombinant

Results in Table 2 show that the 12D10 monoclonal antibody reacts specifically with both factor VII and factor VIIa antigen.

TABLE 3

| Identification of Neutralizing Activity of Hybridoma antibody 12D10 | |
|---|---|
| Inhibitor | Percent Inhibition of F.X Activation |
| Buffer | 0 |
| Anti-tPA Monoclonal Antibody | 3 |
| PPACK (1 μM) | 100 |
| 12D10 (1:10 dilution) | 100 |

Results in Table 3 indicate that the 12D10 monoclonal antibody inhibits activity of the tissue factor:factor VIIa complex.

EXAMPLE 2

The factor X activation assay was used to determine the mechanism of inhibition by the 12D10 monoclonal antibody. Hybridoma culture supernatants diluted 1:50 were preincubated with either rF.VIIa or rF.VIIa (rF.7VIIa and rF.VIIa indicates recombinant source of specified molecule) precomplexed to cellular tissue factor expressed on the surface of J-82 cells. Antibody incubations were for 30 minutes at room temperature. Efficiency of antibody blocking was assessed in the factor X activation assay. Controls included irrelevant hybridoma antibody (anti tPA) and a monoclonal to factor VIIa which is known to prevent the association of tissue factor with factor VIIa but will not inhibit activity following complex formation (Mab 1296). The optimal specificity for an antithrombotic monoclonal antibody is one that inhibits the cellular complex of tissue factor and factor VIIa. Results from this experiment are presented in Table 4.

TABLE 4

| Mechanism on Inhibition of F.VIIa by Hybridoma Antibody 12D10 | | |
|---|---|---|
| Monoclonal Antibody | Preincubation | % Inhibition of F.X Activation |
| 12D10 | F.VIIa | 97 ± 0 |
| 12D10 | TF:VIIa | 98 ± 0 |
| 1296 | F.VIIa | 85 ± 1 |
| 1296 | TF:VIIa | 22 ± 12 |
| anti tPA | F.VIIa | 0 ± 0 |
| anti tPA | TF:F.VIIa | 3 ± 5 |

These results demonstrate the ability of monoclonal antibody 12D10 to inhibit the activity of both free factor VIIa and cellular complexes of tissue factor and factor VIIa, an important property for the disclosed therapeutic anticoagulant.

EXAMPLE 3

Detailed specificity of the 12D10 monoclonal antibody was evaluated as follows. A series of synthetic peptides representing linear sequences from the two gla domains, EGF domains, the light chain and the catalytic site of factor VIIa were tested for reactivity with the 12D10 monoclonal antibody. The experiment was performed by coating microtiter wells with 12D10 monoclonal antibody and reacting the capture antibody with 25 μL of a 100 μM solution of indicated peptide for 30 minutes at 37° C. following this incubation, 25 μL of 1 nM $^{125}$I-factor VIIa was added to each well for one hour at room temperature. Wells were washed and bound $^{125}$I-factor VIIa was determined. Factor VIIa peptide containing amino acid residues 195–208 prevented the binding of the 12D10 monoclonal antibody to $^{125}$I-factor VIIa.

This result was confirmed by direct binding of the 12D10 monoclonal antibody to the Factor VIIa peptide 195–208. Peptides were adsorbed to microtiter wells at a concentration of 1 mg per mL at 37° C. for 2 hours. Wells were blocked with albumin and reacted with 12D10 monoclonal antibody (10 μg per mL) for 2 hours at 37° C. Goat anti-mouse IgG peroxidase conjugate was used to demonstrate bound monoclonal antibody followed by substrate development and determination of OD-450. Peptides representing the gla (2 peptides), EGF (8 peptides), light chain (2 peptides) and catalytic (11 peptides) domains were tested. The catalytic domain peptide 195–208 bound 12D10 monoclonal antibody (OD-450= 0.450) while all others were negative (OD-450≦0.042). The specificity of the 12D10 monoclonal antibody for the catalytic domain of factor VIIa is consistent with our discovery that the antibody binds to VIIa before and after reaction with tissue factor:VII complex.

EXAMPLE 4

Characterization of the activity of F(ab) fragments of 12D10 antibody was carried out as follows. The production of F(ab) fragments of the 12D10 monoclonal antibody was accomplished using a commercial kit (Bioprobe International Tustin, CA). F(ab) fragments are prepared by papain cleavage of IgG. Papain is inhibited and removed by addition of anti-papain polyclonal antibody. Protein A chromatography is used to clear Fc fragments, intact IgG and immune complexes containing papain. The F(ab) fragments were further purified by size exclusion chromatography using a Superose 12 column. Monoclonal antibody 12D10, purified as described above, was analyzed before and after papain digestion. The resulting purity of the 12D10 IgG and F(ab) fragments was about 95%. The activity of these F(ab) fragments was compared to intact 12D10 IgG in both the factor X activation assay and clotting inhibition assays. Analysis of 12D10 IgG and F(ab) fragments in the factor X activation assay was performed as described above, except that optimally relipidated recombinant human tissue factor was substituted for J-82 cells as a source of tissue factor. This modification enhances the precision and the reproducibility of the assay and alleviates the need to perform cell culture to obtain J-82 cells. In these experiments, factor VII and was preincubated for 30 minutes at room temperature with the 12D10 IgG or F(ab) prior to introducing the immune complexes into the factor X activation or clotting assays.

TABLE 5

| Inhibition of F.X Activation With 12D10 IgG and F(ab) | | |
|---|---|---|
| Inhibitor | Molar Ratio of Antibody Binding Sites to Factor VIIa | Percent Inhibition |
| 12D10 IgG | 100 | 100 |
| 12D10 IgG | 10 | 100 |
| 12D10 IgG | 1.0 | 100 |
| 12D10 IgG | 0.1 | 28 |
| 12D10 F(ab) | 100 | 100 |
| 12D10 F(ab) | 10 | 100 |
| 12D10 F(ab) | 1.0 | 100 |
| 12D10 F(ab) | 0.1 | 45 |
| Anti-tPA IgG | 100 | 5 |
| Anti-tPA IgG | 10 | 0 |
| Anti-tPA IgG | 1.0 | 2 |
| Anti-tPA IgG | 0.1 | 0 |

These results, shown in Table 5, indicate that the fragmentation of the 12D10 antibody did not result in a loss of biological activity. Activity of the IgG and F(ab) fragments are essentially identical under these experimental conditions. The potency of the 12D10 antibody is evident from this result as inhibition at 1:1 molar ration of antibody site to enzyme is observed. Inhibition of the factor X activation assay at ratios of factor VIIa:monoclonal less than 1 can be explained by the fact that the assay readout is an extreme amplification of the residual (uninhibited) quantity of factor VIIa activity present in the sample.

EXAMPLE 5

The 12D10 monoclonal antibody will inhibit the clotting of recalcified human plasma in a two stage prothrombin time test. The effect of the F(ab) fragmentation process on this property was analyzed as follows. Plasma was diluted 1:2 with 2 mM sodium citrate. IgG or F(ab) at indicated concentrations (50 μL) was added to 100 μL of diluted plasma and incubation was performed at room temperature for 20 minutes. Human thromboplastin (Thromborel S: Behring Diagnostics) was diluted 1:1000 in 30 mM $CaCl_2$ and 200 μL was added to the plasma/antibody solution.

Figure 2:
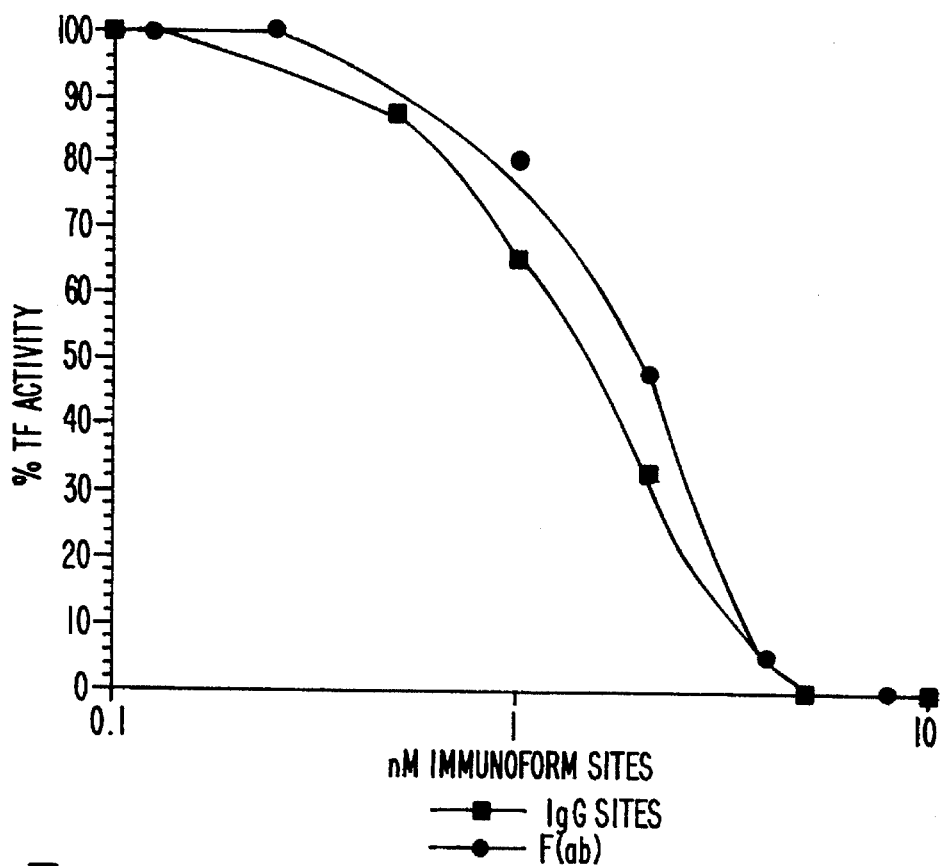
FIG. 2 shows the ability of 12D10 monoclonal antibody and 12D10 F(ab) fragment to inhibit the clotting of recalcified human plasma in a two stage prothrombin time test.

Clotting times were determined in a Coagamate optical coagulometer (Organon Technica). Clotting times are converted to percent tissue factor activity by an algorithm previously described, Hvatum, M. and Prydz H. Studies on Tissue Thromboplastin. Solubilization with Sodium Dioxycholate. Biochem. Biophys. Acta. 130:92–101 (1966). The results are presented in FIG. 2. These results demonstrate that the 12D10 F(ab) fragment is a potent inhibitor of clotting of human plasma.

EXAMPLE 6

The 12D10 monoclonal antibody decreases the level of free factor VII/VIIa antigen upon administration in vivo to a chimpanzee. Such a decreased level of these antigens is maintained for periods in excess of one hour, and in some cases for over five, or even ten hours.

The F(ab) fragment of the 12D10 monoclonal antibody was administered to chimpanzees to assess pharmacokinetics, systemic anticoagulant effect and limited toxicity. Three normal adolescent chimpanzees (45–55kg) were selected for the study. All animals underwent physical examination by a veterinarian including complete blood count (CBC), serum chemistry screen, fecal exam (oocytes and parasites) and hepatitis serological screens. Hematology, coagulation and clinical chemistry parameters were tested and shown to be within normal range. Animals were selected that had no previous exposure to murine proteins, and that were chimp anti-murine antibody (CHAMA) negative.

Animals were intermittently anesthetized with ketamine prior to manipulations. Initially, five doses were selected for administration. Doses that prolonged the prothrombin time were repeated in two additional chimpanzees. Plasma samples were obtained at −15, 15, 30, 60, 120, 240, 360, 1440 and 2880 minutes following administration for evaluation of hematologic, physiologic and coagulation parameters. The study required five weeks with a total of 16 injections of the 12D10 Fab fragment. No immediately observable ill effects were noted; however, some hematoma formation and bleeding back at the site of ketamine injection was observed at the higher doses.

Figure 3:
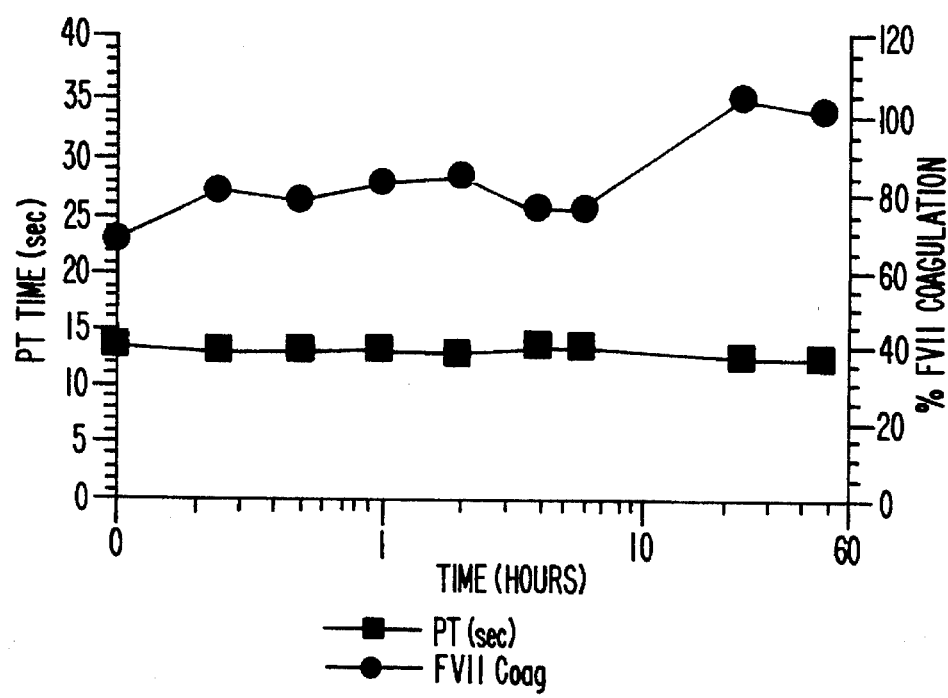
FIG. 3 is a graph showing plasma PT (prothrombin time) and factor VII coagulant activity over time following intravenous administration of 12D10 F(ab) fragment.

Administration of low levels (0.0023–0.0058 mg per kg) had no apparent effect on PT or factor VII activity (both measured using standard assays). FIG. 3 illustrates that PT values and factor VII coagulant activity remain essentially constant following injection with a 0.0035 mg per kg dose of the 12D10 F(ab) fragment.

The threshold for observation of systemic effect was at a dose of 0.04 mg per kg. At this dose level, the prothrombin time was prolonged to greater than 30 seconds, with simultaneous reduction of factor VII coagulant activity and free factor VII/VIIa antigen to less than 10% and less than 10ng per mL, respectively.

Figure 4:
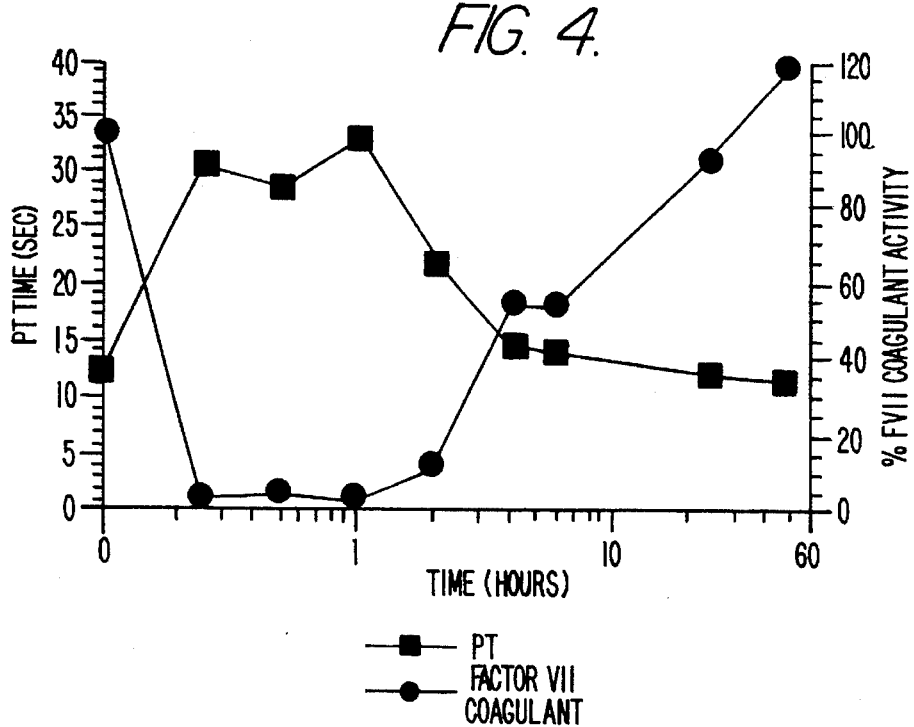
FIG. 4 is a graph showing PT and factor VII coagulant activity over time following intravenous administration of 12D10 F(ab) fragment.
Figure 5:
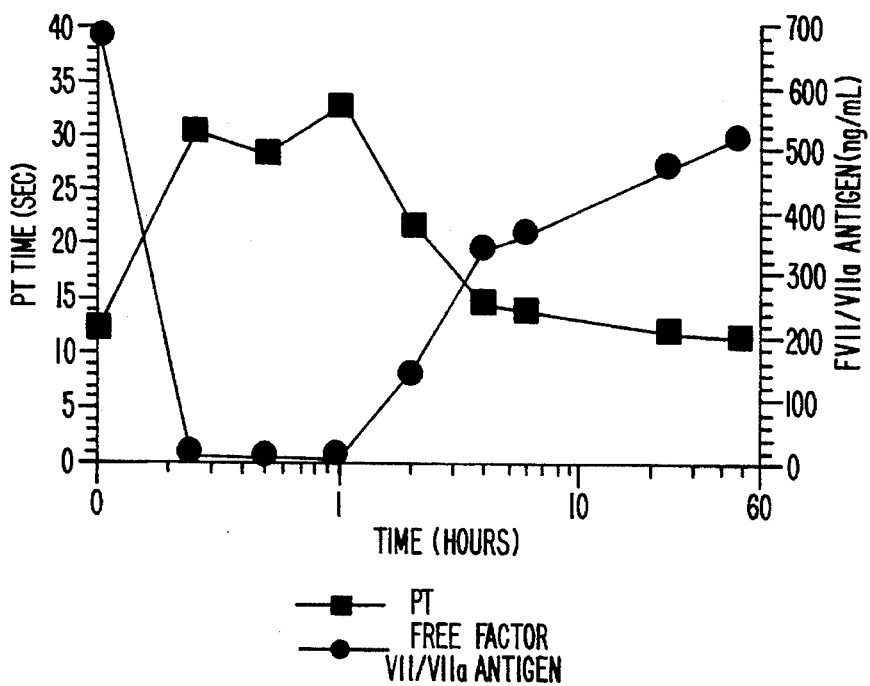
FIG. 5 is a graph showing PT and free factor VII/VIIa antigen over time following intravenous administration of 12D10 F(ab) fragment.

The systemic effect of 12D10 F(ab) fragment on coagulation parameters was observed in a chimpanzee infused intravenously with 0.0547 mg per kg 12D10 F(ab) fragment. In FIG. 4, the rapid increase in plasma PT values was reflected by the concomitant decrease in factor VII coagulant activity. The decrease in free factor VII/VIIa antigen level is demonstrated in FIG. 5.

Figure 6:
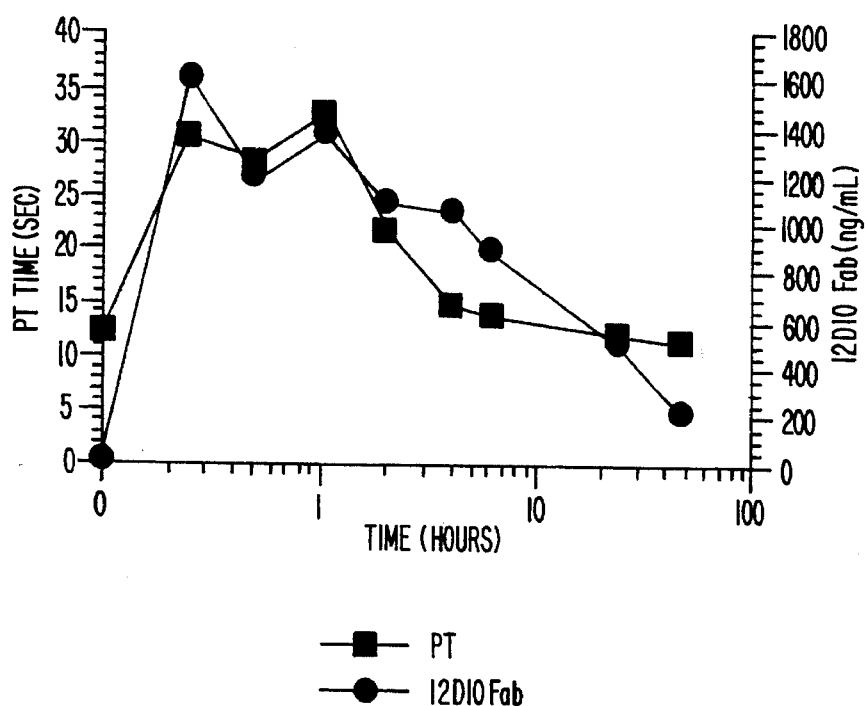
FIG. 6 is a graph showing PT and 12D10 Fab concentration over time following intravenous administration of 12D10 F(ab) fragment.

As factor VII/VIIa antigen and factor VII coagulant levels fell, plasma levels of 12D10 F(ab) fragment increased dramatically in parallel to the PT values over the course of the study. Plasma F(ab) fragment levels appeared to correlate directly with plasma PT values and in reverse with factor VII/VIIa antigen levels. Plasma F(ab) fragment reached peak concentration within the first 15 minutes following injection. The change in plasma levels of 12D10 F(ab) fragment is shown in FIG. 6.

Figure 7:
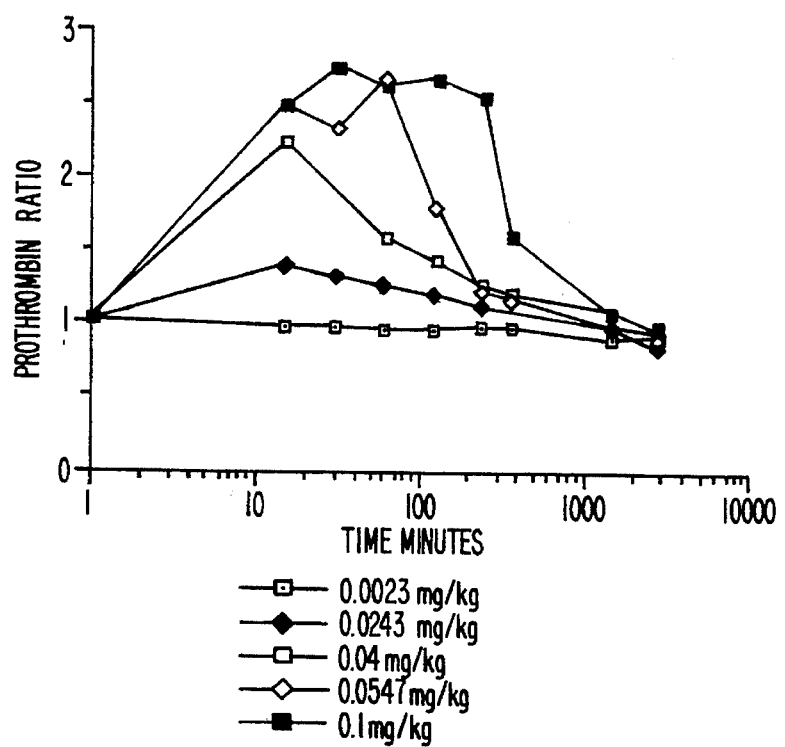
FIG. 7 is a graph showing PT before and after administration of 12D10 F(ab) in a single chimpanzee.

FIG. 7 compares a range of doses that were administered to a single chimpanzee. The duration of response increased with escalating dose level. The duration of response at the 0.1 mg per kg level was approximately double that at the 0.0547 mg per g/kg dose level. A dose escalation effect is also evident from these data. The threshold for this animal appears to be approximately 0.04 mg per kg 12D10 F(ab) fragment.

Other embodiments are within the following claims.

We claim:

1. Monoclonal antibody 12D10 secreted by a cell line as deposited by ATCC Accession No. HB 10558.

2. Functional antigen binding fragments of monoclonal antibody 12D10 secreted by a hybridoma cell line as deposited by ATCC Accession No. HB 10558.

3. Hybridoma cell line ATCC HB 10558.

* * * * *

UNITED STATES PATENT AND TRADEMARK OFFICE
CERTIFICATE OF CORRECTION

PATENT NO. : 5,506,134
DATED : April 9, 1996
INVENTOR(S) : Soule, et al

It is certified that error appears in the above-identified patent and that said Letters Patent is hereby corrected as shown below:

Column 13, Line 24, delete "50λL" and insert -- 50uL --.

Signed and Sealed this

Eighth Day of December, 1998

*Attest:*

BRUCE LEHMAN

*Attesting Officer*     *Commissioner of Patents and Trademarks*